US012471943B2

(12) United States Patent
Pilletere et al.

(10) Patent No.: US 12,471,943 B2
(45) Date of Patent: Nov. 18, 2025

(54) LAPAROSCOPIC TISSUE CUTTING DEVICE

(71) Applicant: Covidien LP, Mansfield, MA (US)

(72) Inventors: Roy J. Pilletere, Middletown, CT (US); Jacob C. Baril, Norwalk, CT (US); Matthew A. Dinino, Newington, CT (US); Justin J. Thomas, New Haven, CT (US); Garrett P. Ebersole, Hamden, CT (US); Saumya Banerjee, Collinsville, CT (US); Nicolette L. Roy, Windsor Locks, CT (US)

(73) Assignee: Covidien LP, Mansfield, MA (US)

( * ) Notice: Subject to any disclaimer, the term of this patent is extended or adjusted under 35 U.S.C. 154(b) by 1073 days.

(21) Appl. No.: 17/498,853

(22) Filed: Oct. 12, 2021

(65) Prior Publication Data

US 2022/0192693 A1 Jun. 23, 2022

Related U.S. Application Data

(60) Provisional application No. 63/126,609, filed on Dec. 17, 2020.

(51) Int. Cl.
*A61B 17/32* (2006.01)

(52) U.S. Cl.
CPC ................. *A61B 17/320016* (2013.01); *A61B 2017/320028* (2013.01)

(58) Field of Classification Search
CPC .......... A61B 17/320016; A61B 17/295; A61B 17/1608; A61B 17/1611; A61B 2017/320016; A61B 2017/320028; A61B 2017/320064; A61B 2017/320092; A61B 2017/2902; A61B 2017/2913; A61B 2017/2919; A61B 2017/2933; A61B 2017/2934; A61B 2017/2938; A61B 2017/2939; A61B 2017/2944; A61B 18/1445; A61B 18/1447
See application file for complete search history.

(56) References Cited

U.S. PATENT DOCUMENTS

| | | | | |
|---|---|---|---|---|
| 6,036,667 | A * | 3/2000 | Manna ........... | A61B 17/320092 606/205 |
| 7,520,886 | B2 | 4/2009 | Surti | |
| 7,871,423 | B2 | 1/2011 | Livneh | |
| 8,945,163 | B2 | 2/2015 | Voegele | |
| 2003/0139757 | A1* | 7/2003 | Lang .................. | A61B 18/1445 606/174 |
| 2004/0220601 | A1* | 11/2004 | Lang .................. | A61B 17/1608 606/205 |
| 2010/0179578 | A1* | 7/2010 | Tannoury ............... | A61B 17/32 600/564 |
| 2013/0190649 | A1* | 7/2013 | Lee ........................ | A61B 10/04 600/567 |
| 2015/0080905 | A1 | 3/2015 | Begemann et al. | |

* cited by examiner

*Primary Examiner* — Diane D Yabut
(74) *Attorney, Agent, or Firm* — Draft Masters IP, LLC

(57) ABSTRACT

A tissue cutting device has a blade that pivots to pierce through tissue and translates to cut tissue, thereby providing a clean and smooth cut through tissue. The blade is coupled to an axial rod. Axial displacement of the axial rod pivots the blade and imparts axial displacement to the blade.

20 Claims, 7 Drawing Sheets

LAPAROSCOPIC TISSUE CUTTING DEVICE

CROSS-REFERENCE TO RELATED APPLICATIONS

This application claims the benefit of and priority to U.S. Provisional Patent Application Ser. No. 63/126,609, filed on Dec. 17, 2020, the entire disclosure of which is incorporated by reference herein.

FIELD

The disclosure relates generally to surgical instruments, and more particularly, to a laparoscopic tissue cutting device.

BACKGROUND

Minimally invasive surgical procedures, including endoscopic, laparoscopic, and arthroscopic procedures, have been used for introducing surgical instruments inside a patient and for viewing portions of the patient's anatomy. Forming a relatively small diameter, temporary pathway to the surgical site is a key feature of most minimally invasive surgical procedures. The most common method of providing such a pathway is by inserting a trocar cannula assembly through the skin. The trocar cannula assembly may include an expandable balloon configured to enhance securement of the trocar cannula assembly in an opening in tissue.

When compared to the larger openings typically found in traditional procedures, both trauma to the patient and recovery time are reduced for procedures involving small openings. However, minimally invasive surgery has several limitations. In particular, surgery of this type including, e.g., cutting of tissue, requires a great deal of skill in manipulating the long narrow endoscopic instruments to a remote site under endoscopic visualization. Therefore, there is a need in the art for an improved surgical instrument for cutting tissue.

SUMMARY

In accordance with the disclosure, a tissue cutting device includes an elongate shaft assembly, an actuation assembly, and a blade assembly. The elongate shaft assembly includes an elongate shaft defining first and second lumens and a support extending distally from the elongate shaft. The actuation assembly includes a pivoting rod slidably extending through the first lumen and an axial rod slidably extending through the second lumen of the elongate shaft. The blade assembly includes a blade to cut tissue and a body supporting the blade. The body includes a camming portion slidably engaging the support of the elongate shaft assembly. The body is operatively coupled to the pivoting rod and the axial rod of the actuation assembly. A first axial displacement of the axial rod pivots the blade between a closed configuration, in which, a distal portion of the blade engages the support of the elongate shaft assembly, and an open configuration, in which, the blade is pivoted to receive tissue between the blade and the support. A second axial displacement of the axial rod imparts concomitant axial displacement to the blade assembly to cut tissue.

In an aspect, the actuation assembly may further include a spring operatively associated with the pivoting rod to bias the axial rod towards a distal-most position.

In another aspect, the support of the elongate shaft assembly may have a planar portion and an arcuate portion conforming to a curvature of the elongate shaft.

In yet another aspect, the planar portion may define a groove having first and second portions. The first portion may be configured to receive the distal portion of the blade. The second portion may be configured to receive the camming portion of the body of the blade assembly.

In still yet another aspect, the second lumen of the elongate shaft may be in communication with the groove of the planar portion.

In still yet another aspect, the second lumen of the elongate shaft may be axially aligned with the groove of the planar portion.

In still yet another aspect, the first lumen of the elongate shaft may be radially spaced apart from the second lumen of the elongate shaft.

In an aspect, the second portion of the groove may be in superposed relation with the first portion of the groove.

In another aspect, the support of the elongate shaft assembly may have a semicylindrical shape.

In yet another aspect, the blade may have a substantially L-shaped profile.

In an aspect, the blade may have an arcuate portion to engage tissue.

In accordance with another aspect of the disclosure, a tissue cutting device includes an elongate shaft assembly, an actuation assembly, and a blade assembly. The elongate shaft assembly includes an elongate shaft and a support extending distally from the elongate shaft. The actuation assembly includes a pivoting rod and an axial rod slidably extending through the elongate shaft. The pivoting rod is in superposed relation with the axial rod. The blade assembly includes a blade having a pointed tip and a body supporting the blade and slidably engaging the support of the elongate shaft assembly. The body is operatively coupled to the pivoting rod and the axial rod such that axial displacement of the axial rod pivots the blade to pierce through tissue and imparts axial displacement to the blade to cut tissue.

In an aspect, the blade may have an arcuate shape.

In another aspect, the blade assembly may be pivotable between an aligned position, in which, the blade assembly is aligned with the elongate shaft, and an offset position, in which, the blade assembly is offset from the elongate shaft.

In yet another aspect, the pivoting rod of the actuation assembly may be coupled to a spring to bias the blade towards an open configuration.

In still yet another aspect, the support may have a semi-cylindrical shape.

In an aspect, the support may define a groove to slidably receive a portion of the body of the blade assembly therein.

In another aspect, the body may include a pivot pin extending traversely outwards to pivotably engage bores defined in a distal portion of the pivoting rod and may define a bore to receive a support pin of the axial rod therein.

In accordance with yet another aspect of the disclosure, a tissue cutting device includes an elongate shaft assembly, an actuation assembly, and a blade assembly. The elongate shaft assembly includes a shaft and a support extending distally from the shaft. The actuation assembly includes a pivoting rod and an axial rod slidably extending through the shaft of the elongate shaft assembly. The blade assembly includes a blade configured to cut tissue and a body supporting the blade. The body is operatively coupled to the axial rod such that axial displacement of the axial rod of the actuation assembly pivots the blade to pierce through tissue and imparts axial displacement to the blade to cut tissue.

In an aspect, axial displacement of the axial rod may pivot the blade assembly about a pivot disposed on the body and the axial rod may be coupled to the body at the pivot.

BRIEF DESCRIPTION OF DRAWINGS

A tissue cutting device is disclosed herein with reference to the drawings, wherein.

DETAILED DESCRIPTION

Figure 1:
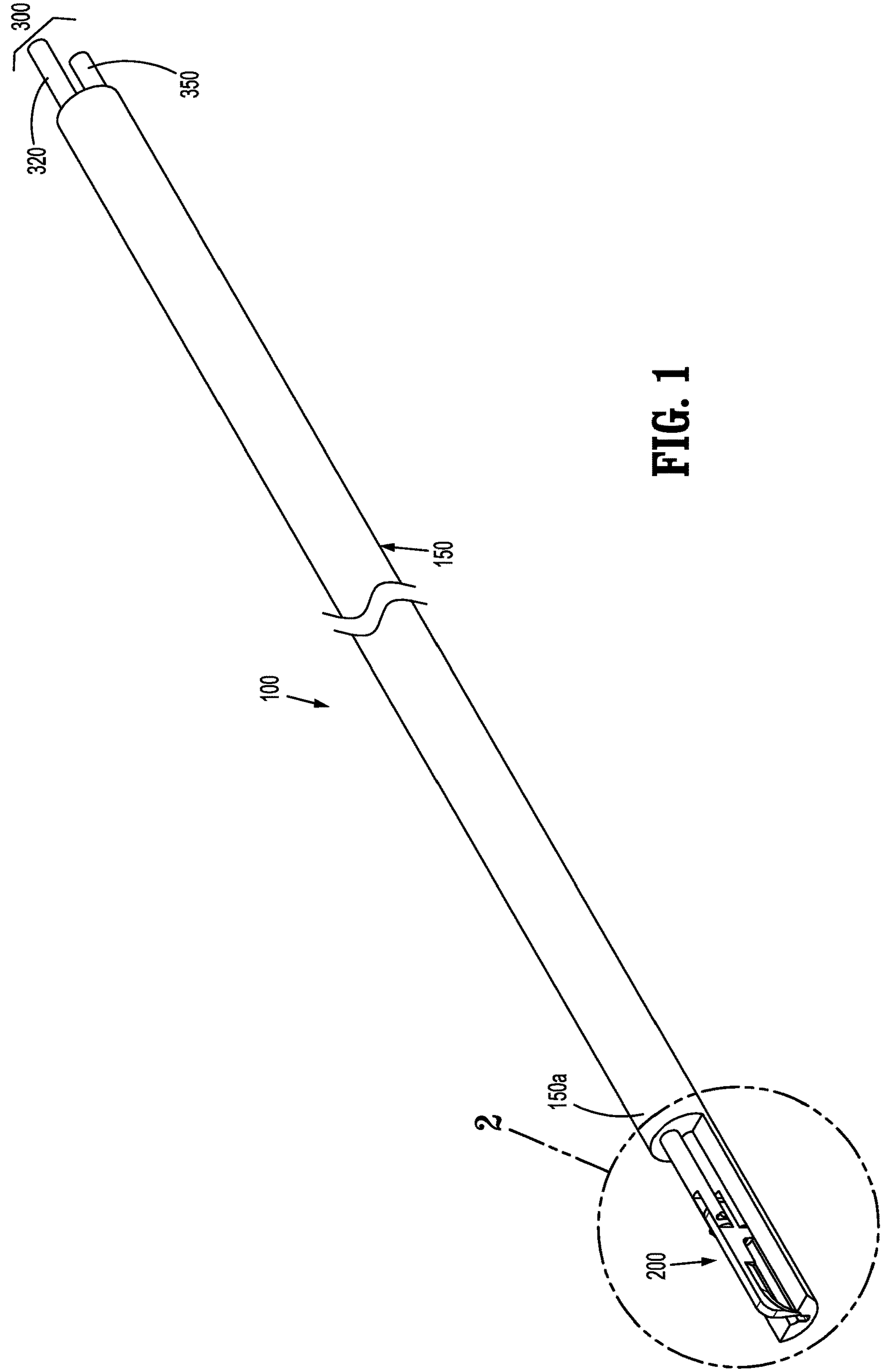
FIG. 1 is a perspective view of a tissue cutting device in accordance with the disclosure.

A laparoscopic tissue cutting device is described in detail with reference to the drawings, wherein like reference numerals designate corresponding elements in each of the several views. As used herein, the term "distal" refers to that portion of the instrument, or component thereof which is farther from the user while the term "proximal" refers to that portion of the instrument or component thereof which is closer to the user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 2:
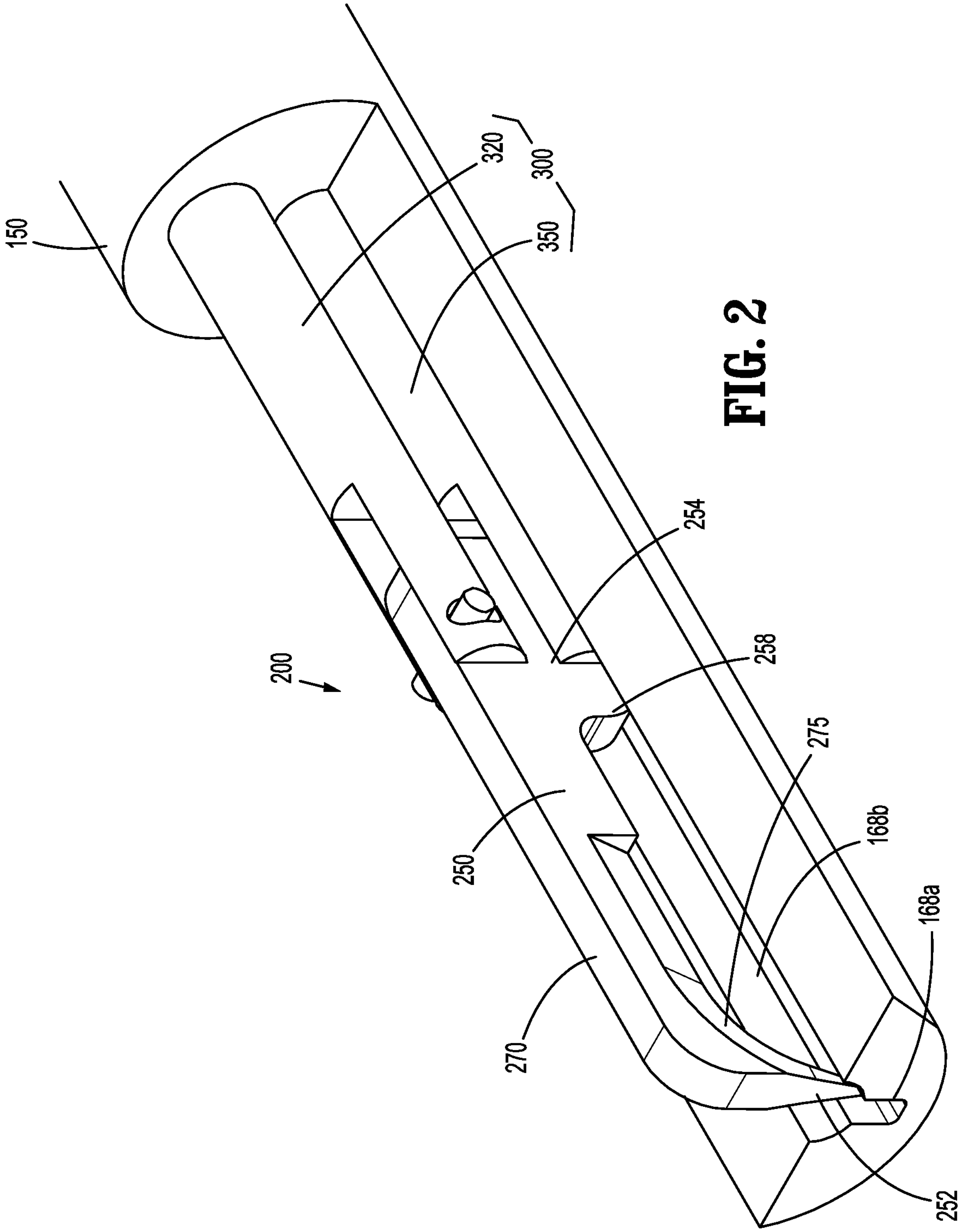
FIG. 2 is an enlarged perspective view of the indicated area of detail of FIG. 1.

FIGS. 1 and 2 illustrate a laparoscopic tissue cutting device shown generally as a tissue cutting device 100. The tissue cutting device 100 provides a smoother cut through tissue and a longer lasting blade than conventional surgical scissors. The tissue cutting device 100 includes an elongate shaft assembly 150, a tool assembly 200 supported on a distal end portion **150*a* of the elongate shaft assembly 150, and an actuation assembly 300 (FIG. 3) extending through the elongate shaft assembly 150 and operatively coupled to the tool assembly 200. The tool assembly 200 is configured to cut tissue by enabling a distal tip portion 252 of a blade assembly 250 of the tool assembly 200 to pivotably penetrate tissue and retracting the blade assembly 250** to slice tissue, thereby providing a clean and smooth cut through tissue, as will be discussed below.

Figure 3:
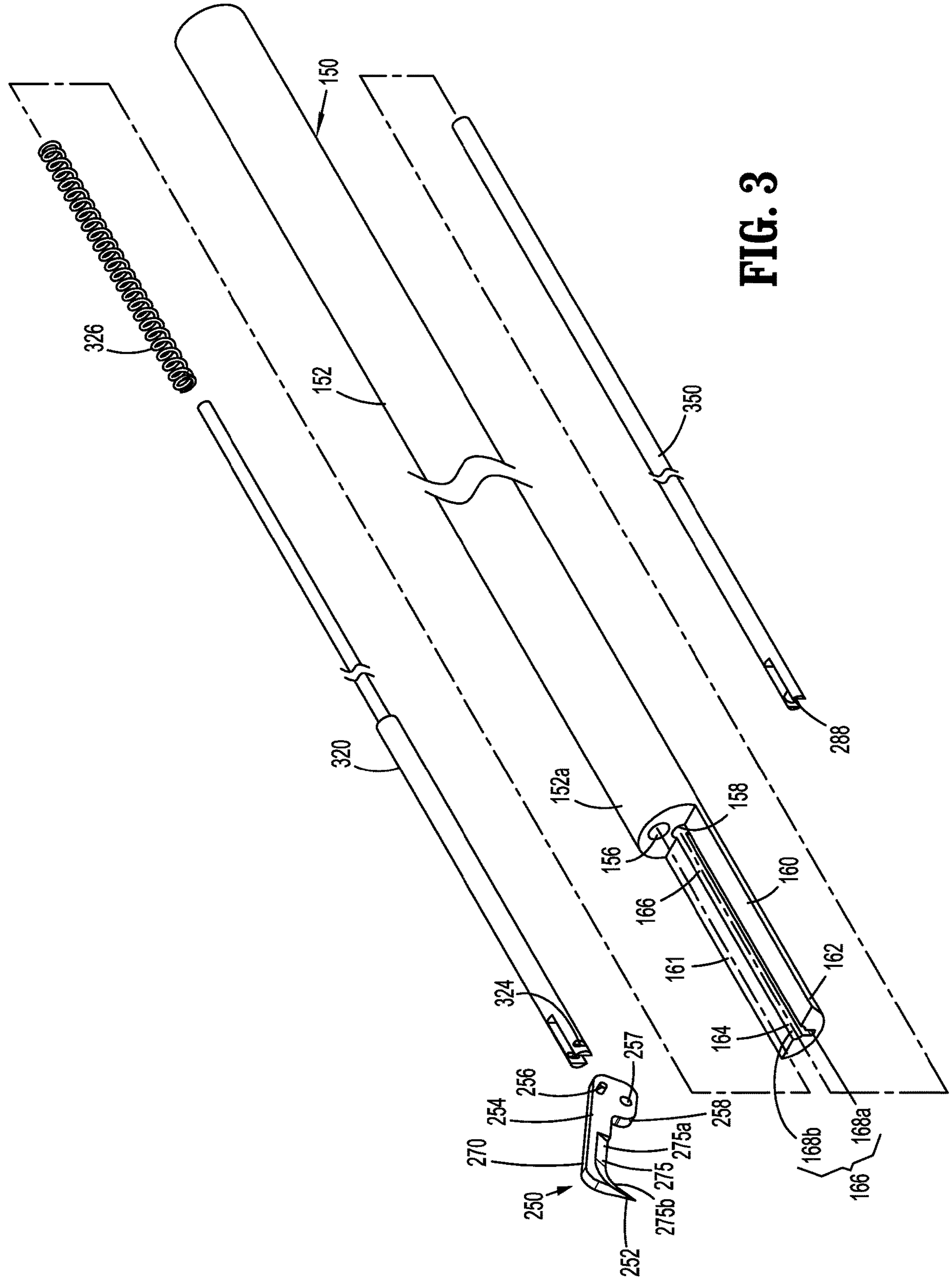
FIG. 3 is an exploded perspective view of the tissue cutting device of FIG. 1 with parts separated.

FIG. 3 illustrates the elongate shaft assembly 150 including a shaft 152 and a support 160 extending distally from the distal end portion **152*a* of the shaft 152. The elongate shaft assembly 150 is configured to receive a pivoting rod 320 and an axial rod 350 of the actuation assembly 300 therethrough. In particular, the shaft 152 defines first and second lumens 156, 158 extending through the shaft 152. The first and second lumens 156, 158 are dimensioned to receive the pivoting rod 320 and the axial rod 350, respectively. The first and second lumens 156, 158** are radially spaced apart.

The support 160 of the elongate shaft assembly 150 includes an engaging portion 161 configured to operatively engage the blade assembly 250 of the tool assembly 200, and an arcuate portion 162 conforming to a curvature of the shaft 152 to facilitate insertion through, e.g., an opening in tissue or a lumen 1510 (FIG. 10) of a cannula assembly 1500. For example, the support 160 may have a semicylindrical shape. The engaging portion 161 may include a planar surface 164 and define a groove 166. The groove 166 has a first portion **168*a* dimensioned to receive the distal tip portion 252 of the blade assembly 250 and a second portion 168*b* dimensioned to receive a camming portion 258 of the blade assembly 250. The second portion 168*b* is coterminous with the planar surface 164 of the engaging portion 161 and extends towards the arcuate portion 162. The first portion 168*a* of the groove 166 is in communication with the second portion 168*b*. In this manner, the second portion 168*b* of the groove 166 is in superposed relation with the first portion 168*a*. In addition, the groove 166 is in communication with and axially aligned with the second lumen 158 of the shaft 152**.

FIGS. 2 and 3 illustrate the blade assembly 250 including a body 254, a neck portion 270 extending distally from the body 254, and a distal tip portion 252 substantially orthogonal to the neck portion 270. In particular, the body 254 has a pivot pin 256 extending transversely outwards from opposing sides of the body 254 and defines a bore 257. The pivot pin 256 is coupled to the pivoting rod 320 of the actuation assembly 300. The bore 257 is dimensioned to receive a support pin 288 of the axial rod 350. The pivot pin 256 and the bore 257 are disposed on the body 254 of the blade assembly 250 to enable pivoting of the blade assembly 250 about the bore 257, as will be discussed below.

The body 254 of the blade assembly 250 has the camming portion 258 configured to be slidably received in the second portion **168*b* of the groove 166 of the support 160 for axial displacement through the second portion 168*b* of the groove 166. The neck portion 270 supports a blade 275 configured to cut tissue. The blade 275 includes an elongate portion 275*a* and a distal portion 275*b*. The elongate portion 275*a* of the blade 275 extends along a length of the neck portion 270. The distal portion 275*b* extends towards the distal tip portion 252 of the blade assembly 250 such that the distal portion 275*b* is substantially orthogonal to the elongate portion 275*a*. Under such a configuration, the blade 275 defines a substantially L-shaped or hook profile to facilitate cutting of tissue. In particular, the distal portion 275*b* of the blade 275 may be tapered to facilitate insertion thereof into tissue. The elongate portion 275*a* and the distal portion 275*b* may be connected to define a curvature to further facilitate cutting of tissue. The distal tip portion 252 is configured to be received through the first portion 168*a* of the groove 166 of the support 160**.

Figure 4:
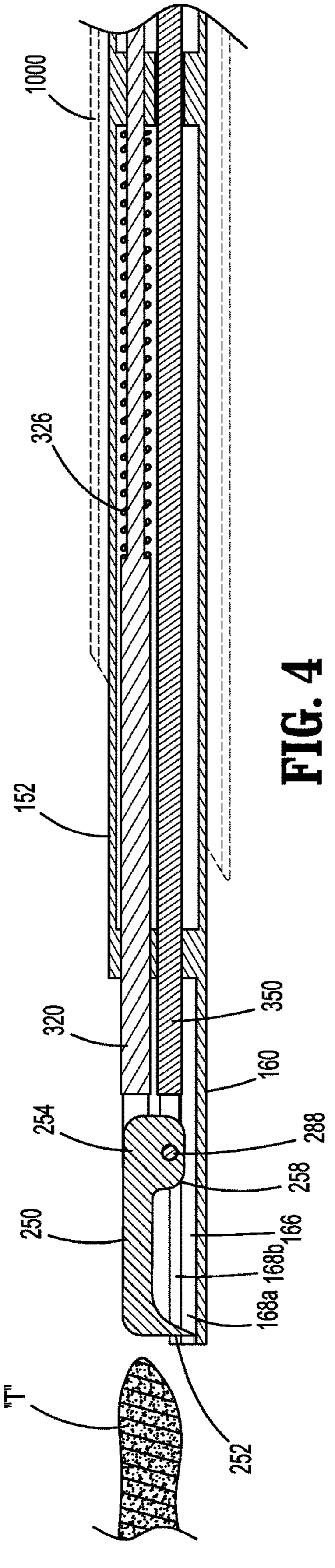
FIG. 4 is a partial side cross-sectional view of the tissue cutting device of FIG. 1, illustrating a tool assembly of the tissue cutting device in a closed configuration.
Figure 5:
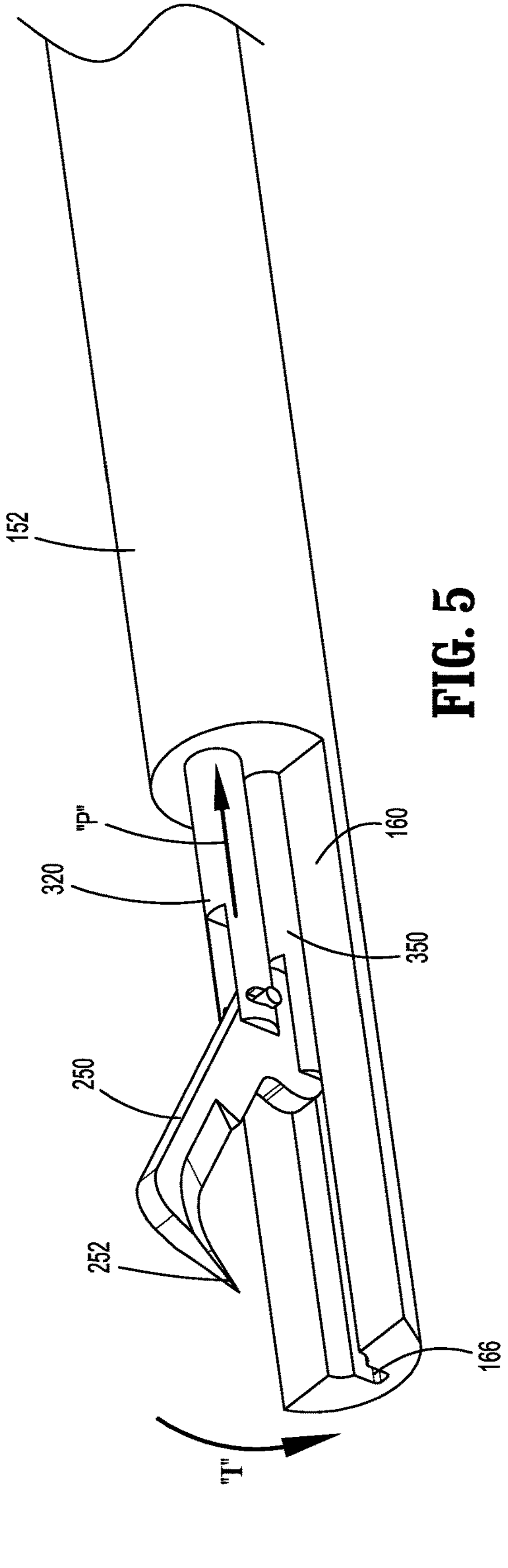
FIG. 5 is a partial perspective view of the tissue cutting device of FIG. 1, illustrating the tool assembly in an open configuration.

FIGS. 3 and 4 further illustrate the pivoting rod 320 defining bores 324 to receive pivot pin 256 of the body 254 of the blade assembly 250 to enable pivoting of the blade assembly 250 about the bore 257 of the body 254. The pivoting rod 320 may further include a spring 326 to bias the axial rod 350 towards a distal-most position such that the blade assembly 250 is offset from the shaft 152 as shown in FIG. 5. Under such a configuration, the distal tip portion 252 of the blade assembly 250 is spaced apart from the support 160. In addition, the support pin 288 of the axial rod 350 of the elongate shaft assembly 150 is received in the bore 257 of the body 254 of the blade assembly 250.

FIG. 5 illustrates the axial rod 350 biased towards the distal-most position such that the blade assembly 250 is in an open configuration. The blade assembly 250 may be transitioned to a closed configuration through retraction of the axial rod 350. Specifically, retraction of the axial rod 350 in the direction of an arrow "P" causes the blade assembly 250 to pivot about the bore 257 (FIG. 3) of the body 254. The distal tip portion 252 of the blade assembly 250 rotates towards the groove 166 of the support 160 in the direction of an arrow "I."

Figure 6:
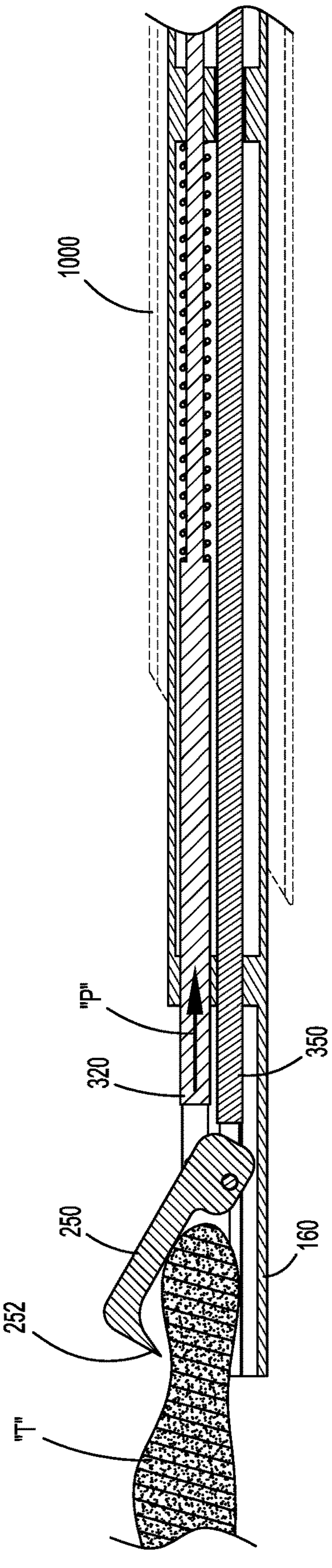
FIG. 6 is a partial side cross-sectional view of the tissue cutting device of FIG. 1, illustrating positioning tissue between the tool assembly and a support of the elongate shaft assembly of the tissue cutting device.
Figure 7:
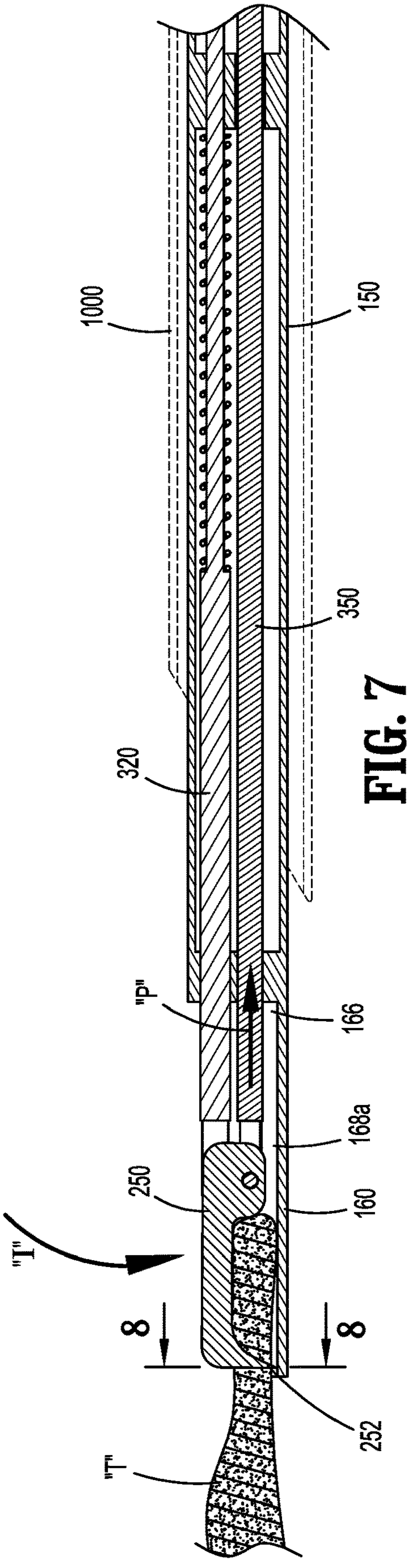
FIG. 7 is a partial side cross-sectional view of the tissue cutting device of FIG. 6, illustrating a distal tip portion of the tool assembly piercing through tissue.

FIG. 6 illustrates placing tissue "T" between a gap defined between the support 160 and the blade assembly 250 in the open configuration. FIG. 7 illustrates the blade assembly 250 in a closed configuration. In this configuration, the blade assembly 250 is aligned with the shaft 152 of the elongate shaft assembly 150. In particular, axial displacement of the axial rod 350 in the direction of the arrow "P" rotates the blade assembly 250 in the direction of an arrow "I". At this time, the distal tip portion 252 of the blade assembly 250 pierces through tissue "T" and is received in the first portion 168*a* of the groove 166 of the support 160 Further, the camming portion 258 of the body 254 of the blade assembly 250 is disposed in the second portion 168*b* of the groove 166.

Figure 8:
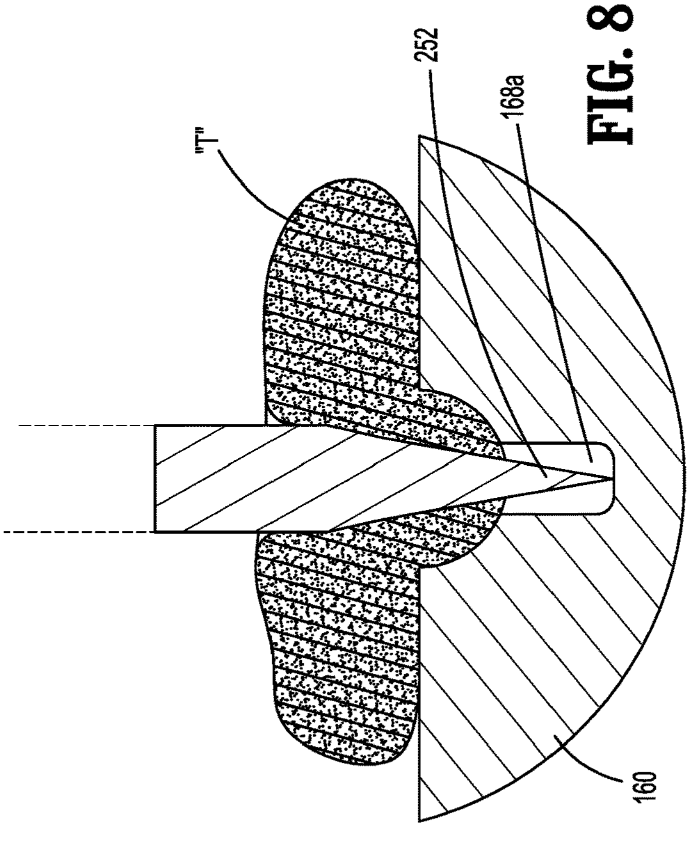
FIG. 8 is a cross-sectional view of the tissue cutting device of FIG. 7 taken along section line 8-8 of FIG. 7.
Figure 9:
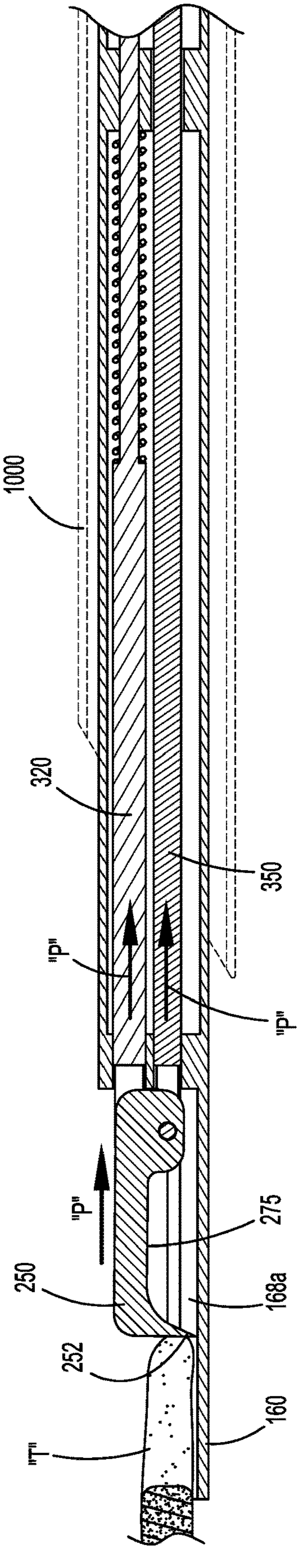
FIG. 9 is a partial cross-sectional view the tissue cutting device of FIG. 1, illustrating cutting of tissue.

FIGS. 8 and 9 illustrate cutting of tissue "T" through further retraction of the axial rod 350 in the direction of the arrows "P". As the axial rod 350 is further retracted in the direction of the arrows "P", the blade 275 piercing through tissue "T" is displaced proximally in the direction of the arrow "P" and the blade 275 severs tissue disposed on the support 160.

Figure 10:
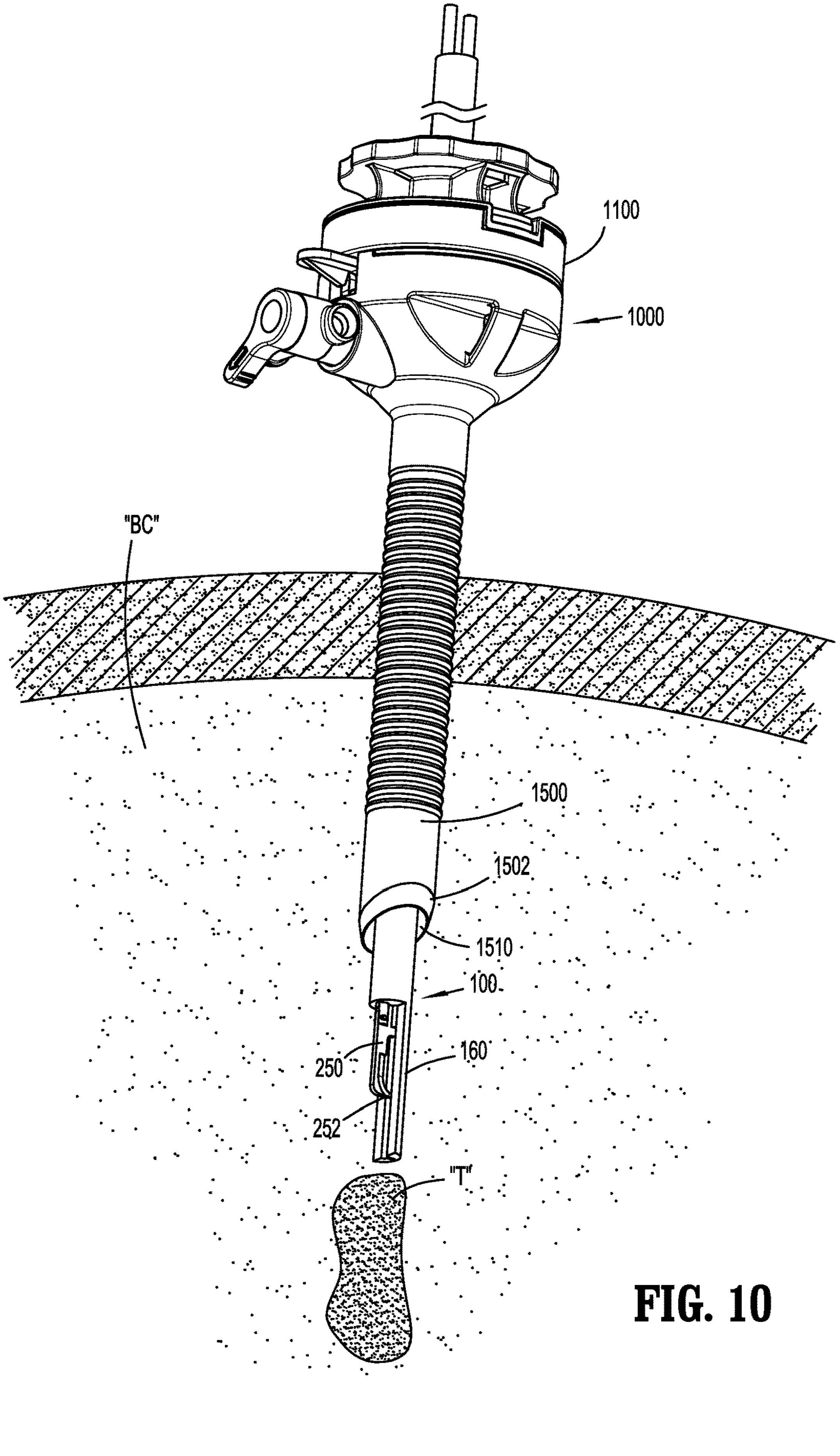
FIG. 10 is a perspective view of the tissue cutting device of FIG. 1, illustrating use thereof in conjunction with a cannula assembly inserted into a body cavity.

FIG. 10 illustrates use of the tissue cutting device 100 in conjunction with a cannula assembly 1000. The cannula assembly 1000 includes a cannula housing 1100 and a cannula member 1500 extending from the cannula housing 1100. The cannula housing 1100 is dimensioned for engagement by the clinician and may include one or more internal seals adapted to establish a seal about a surgical object introduced therethrough. The internal seals may include, e.g., a duck bill or zero-closure seal positioned in the cannula housing 1100. For example, the zero-closure seal may be formed of a suitable resilient material (e.g., silicone) and be configured to inhibit fluids from exiting proximally through the cannula housing 1100 in the absence of a surgical object such as, e.g., the tissue cutting device 100, inserted therethrough. The cannula housing 1100 and the cannula member 1500 may be integrally formed as a single construct.

Initially, an incision is made in a body wall to gain entry to a body cavity, such as the abdominal cavity. The distal portion 1502 of the cannula member 1500 is inserted through the incision. At this time, the body cavity may be insufflated with $CO_2$, a similar gas, or another insufflation fluid. Surgical instruments may be inserted through the cannula assembly 1000 to perform desired surgical procedures. During the surgical procedure, the tissue cutting device 100 may be inserted through the cannula assembly 1000 to cut tissue. In particular, the tool assembly 200 of the tissue cutting device 100 is placed in the closed configuration to facilitate insertion through the cannula assembly 1000. After the tool assembly 200 is inserted through the incision and placed within the body cavity "BC," the tool assembly 200 is placed adjacent target tissue "T". Thereafter, the tool assembly 200 is transitioned to the open configuration to receive tissue "T" between the support 160 of the elongate shaft assembly 150 and the blade assembly 250. Thereafter, the axial rod 350 is retracted such that the distal tip portion 252 of the blade assembly 250 pierces through tissue "T". Thereafter, the axial rod 350 is further retracted to slice tissue disposed on the support 160. The clinician may repeat this process as needed to cut tissue "T".

It is further contemplated that the cannula assembly 1000 may be used with an obturator. The obturator generally includes a head portion having latches configured to engage respective notches defined in the cannula housing 1100 of the cannula assembly 1000 to enhance securement therewith, an elongate shaft extending from the head portion, and an optical penetrating tip coupled to a distal end of the elongate shaft. The optical penetrating tip may be used to penetrate the skin and access the body cavity. By applying pressure against the proximal end of the obturator, the tip of the obturator is forced though the skin and the underlying tissue layers until the cannula and obturator enter the body cavity.

It is also envisioned that the actuation assembly 350 may be operatively coupled to a handle assembly known by one skilled in the art to enable the clinician to actuate the tool assembly 200. It is contemplated that the handle assembly may be a powered or electromechanical handle assembly. It is further envisioned that the tissue cutting device 100 may be configured to connect to a robotic arm of a robotic surgical system to enable manipulation and control thereof. It is to be understood, therefore, various other changes and modifications may be effected therein by one skilled in the art without departing from the scope or spirit of the disclosure.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A tissue cutting device comprising:

an elongate shaft assembly including:
- an elongate shaft defining first and second lumens; and
- a support extending distally from the elongate shaft;

an actuation assembly including:
- a pivoting rod slidably extending through the first lumen; and
- an axial rod slidably extending through the second lumen of the elongate shaft; and a blade assembly including:
- a blade to cut tissue; and
- a body supporting the blade, the body including a camming portion slidably engaging the support of the elongate shaft assembly, the body operatively coupled to the pivoting rod and the axial rod of the actuation assembly, wherein a first axial displacement of the axial rod pivots the blade between a closed configuration, in which, a distal portion of the blade engages the support of the elongate shaft assembly, and an open configuration, in which, the blade is pivoted to receive tissue between the blade and the support, and wherein a second axial displacement of the axial rod imparts concomitant axial displacement to the blade assembly to cut tissue.

2. The tissue cutting device according to claim 1, wherein the actuation assembly further includes a spring operatively associated with the pivoting rod to bias the axial rod towards a distal-most position.

3. The tissue cutting device according to claim 2, wherein the support of the elongate shaft assembly has a planar portion and an arcuate portion conforming to a curvature of the elongate shaft.

4. The tissue cutting device according to claim 3, wherein the planar portion defines a groove having first and second portions, the first portion configured to receive the distal portion of the blade, the second portion configured to receive the camming portion of the body of the blade assembly.

5. The tissue cutting device according to claim 4, wherein the second lumen of the elongate shaft is in communication with the groove of the planar portion.

6. The tissue cutting device according to claim 4, wherein the second lumen of the elongate shaft is axially aligned with the groove of the planar portion.

7. The tissue cutting device according to claim 4, wherein the second portion of the groove is in superposed relation with the first portion of the groove.

8. The tissue cutting device according to claim 1, wherein the first lumen of the elongate shaft is radially spaced apart from the second lumen of the elongate shaft.

9. The tissue cutting device according to claim 1, wherein the support of the elongate shaft assembly has a semicylindrical shape.

10. The tissue cutting device according to claim 1, wherein the blade has a substantially L-shaped profile.

11. The tissue cutting device according to claim 1, wherein the blade has an arcuate portion to engage tissue.

12. A tissue cutting device comprising:

an elongate shaft assembly including:

an elongate shaft; and a support extending distally from the elongate shaft;

an actuation assembly including a pivoting rod and an axial rod, each of the pivoting rod and the axial rod slidably extending through the elongate shaft, the pivoting rod in superposed relation with the axial rod; and a blade assembly including:

a blade having a pointed tip; and a body supporting the blade and slidably engaging the support of the elongate shaft assembly, the body operatively coupled to the pivoting rod and the axial rod such that axial displacement of the axial rod pivots the blade to pierce through tissue and imparts axial displacement to the blade to cut tissue.

13. The tissue cutting device according to claim 12, wherein the blade has an arcuate shape.

14. The tissue cutting device according to claim 12, wherein the blade assembly is pivotable between an aligned position, in which, the blade assembly is aligned with the elongate shaft, and an offset position, in which, the blade assembly is offset from the elongate shaft.

15. The tissue cutting device according to claim 12, wherein the pivoting rod of the actuation assembly is coupled to a spring to bias the blade towards an open configuration.

16. The tissue cutting device according to claim 12, wherein the support has a semicylindrical shape.

17. The tissue cutting device according to claim 16, wherein the support defines a groove to slidably receive a portion of the body of the blade assembly therein.

18. The tissue cutting device according to claim 12, wherein the body includes a pivot pin extending transversely outwards to pivotably engage bores defined in a distal portion of the pivoting rod, and defines a bore to receive a support pin of the axial rod therein.

19. A tissue cutting device comprising:

an elongate shaft assembly including a shaft and a support extending distally from the shaft;

an actuation assembly including a pivoting rod and an axial rod slidably extending through the shaft of the elongate shaft assembly, the axial rod having a support pin extending therefrom; and a blade assembly including:

a blade configured to cut tissue; and a body supporting the blade, the body defining a bore and including a pivot pin extending outwards therefrom, the pivot pin configured to engage at least one bore of the pivoting rod to operatively couple the body of the blade to the pivoting rod, the support pin of the axial rod configured to engage the bore of the body to operatively couple the body to the axial rod such that axial displacement of the axial rod of the actuation assembly pivots the blade to pierce through tissue and imparts axial displacement to the blade to cut tissue.

20. The tissue cutting device according to claim 19, wherein axial displacement of the axial rod pivots the blade assembly about a pivot disposed on the body, and wherein the axial rod is coupled to the body at the pivot.

* * * * *